United States Patent [19]

Ger

[11] Patent Number: 4,586,614

[45] Date of Patent: May 6, 1986

[54] APPARATUS AND METHOD FOR ORGANIZING SUTURE MATERIALS AND MONITORING SUTURE NEEDLES

[76] Inventor: Ralph Ger, 16 Oaks Hunt Rd., Lake Success, N.Y.

[21] Appl. No.: 525,309

[22] Filed: Aug. 22, 1983

[51] Int. Cl.$^4$ ............................................. A47F 5/02
[52] U.S. Cl. ..................................... 211/41; 206/370; 211/70; 211/163
[58] Field of Search ................. 211/70, 70.6, 60.1, 211/41, 144, 163; 206/361, 366, 367, 370, 380; 312/135

[56] References Cited

U.S. PATENT DOCUMENTS

| | | | |
|---|---|---|---|
| 517,342 | 3/1894 | Irwin | 312/135 |
| 2,043,841 | 6/1936 | Stevens | 211/60.1 |
| 3,003,648 | 10/1961 | LaVigne | 211/144 |
| 4,232,784 | 11/1980 | Hesselgren | 206/370 X |
| 4,243,140 | 1/1981 | Thrun | 206/380 |
| 4,342,391 | 8/1982 | Schainholz | 211/70.6 X |

Primary Examiner—Robert W. Gibson, Jr.
Attorney, Agent, or Firm—J. David Dainow

[57] ABSTRACT

A suture organizer apparatus for use with sealed packets of surgical needles and sutures, opened packets for said needles and sutures, and used needles, the apparatus formed as a housing comprising three sections separated from each other by walls, with at least first and second compartments in each section, each compartment in said third section comprising walls defining a space with an opening and an absorbent material traversing said space, said material being impalable to cling to a needle impaled therein.

12 Claims, 5 Drawing Figures

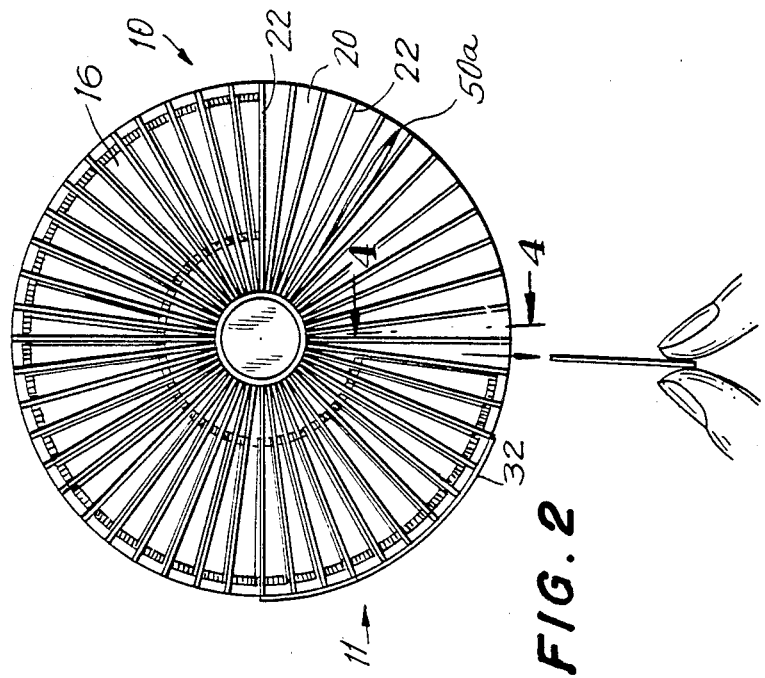
FIG. 5
FIG. 2
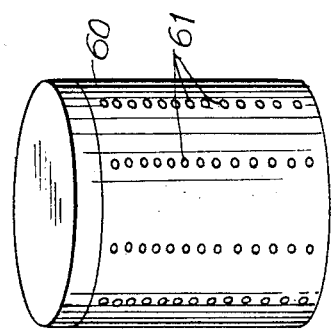
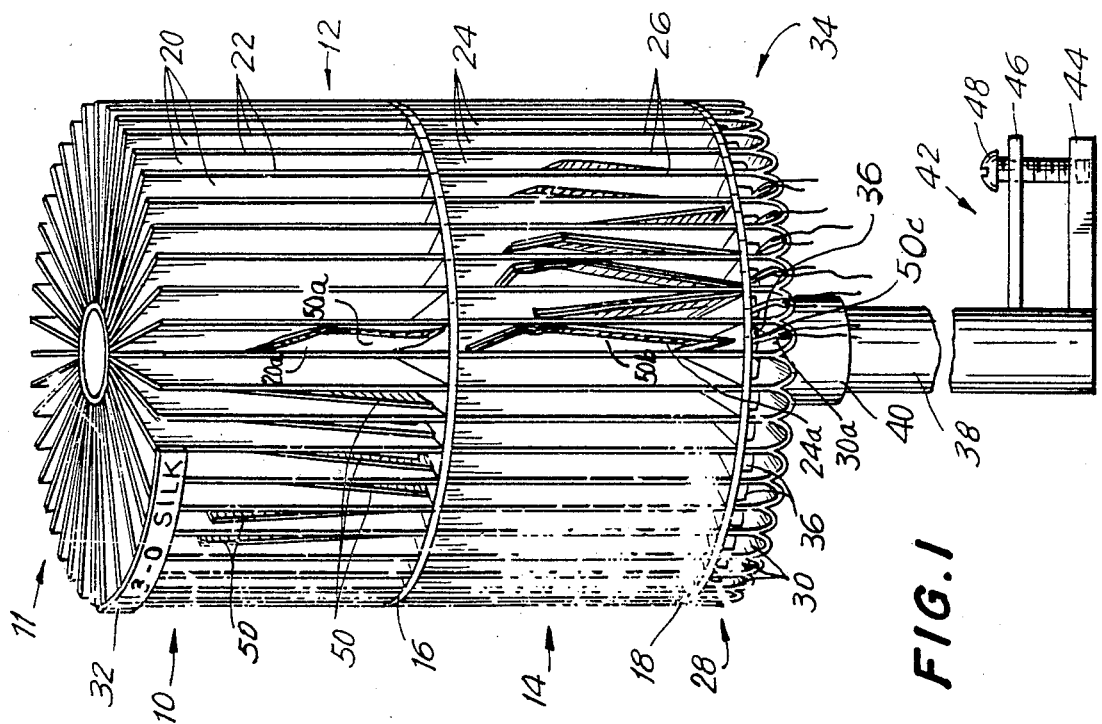
FIG. 1

APPARATUS AND METHOD FOR ORGANIZING SUTURE MATERIALS AND MONITORING SUTURE NEEDLES

TECHNICAL FIELD

The present invention is in operating room equipment and more specifically in an apparatus and method for organizing suture materials and monitoring needles in a hospital or operating room environment.

BACKGROUND OF THE INVENTION

In many operating room (O.R.) environments, the suture arrangements and management are handled primarily by a scrub nurse. Even though several guide lines for monitoring suture needles are followed, generally speaking the processes are imprecise and often lead to a situation where it is difficult or impossible to account for all the needles.

Sutures attached to their needles are kept on the general tray in the O.R. with a considerable amount of other equipment but without consistent arrangement or organization. Presently the usual approach is to place the sutures and attached needles in between folded towels after each has been removed from its packet. The needles are sometimes impaled into the towels to prevent them from being dislodged on the tray. Such impalement usually contributes to blunting the needle tips thus reducing their performance. The needles with their sutures are eventually handed to the surgeon who, after suturing, returns the needles which are finally impaled on a board. The packets from which the needles are taken are usually discarded.

Typically, the circulating nurse, who documents and brings the suture packets to the scrub nurse, is responsible for the needle count. At times the circulating nurse services more than one operating room or often has to leave the O.R. to obtain other equipment. The scrub nurse then cannot obtain additional sutures should they be required, because she cannot break her sterility. In this situation either the operation has to be halted until the circulating nurse returns or another member of the operating room personnel, usually the anesthetist, will obtain the sutures for the scrub nurse; the latter cannot note this in the chart. The scrub nurse is relied upon to tell the circulating nurse of the additional needles used; however, if the procedure is particularly absorbing, the message may not be given.

In an effort to minimize confusion on the scrub nurse's tray, only a relatively small selection of suture materials are provided. Accordingly, the tray is resupplied with sutures as they are required by the circulating nurse who is therefore depended upon to provide proper suture material and to tally the needles. The circulating nurse has other duties which may delay her supplying the suture material and thus delay the operation. Finally opened suture material is discarded at the end of surgery, as it has lost its sterility, and in a busy O.R., this cost is considerable.

DISCLOSURE OF THE INVENTION

The present invention is in an apparatus and method for improving the supplying and monitoring of sutures and needles, for minimizing confusion on scrub tray, for supplying a more than adequate number of sutures to avoid operative delay, and to save the considerable waste incurred by the discarding of opened suture material.

By the new invention a suture packet organizer apparatus is provided which is divided into a plurality of sections, each section being further divided into a plurality of compartments. Blade-like partitions define the separate compartments forming, for example, a first compartment in the first section and an aligned first compartment in the second section. A predetermined number, which may be one or more, of suture packets are placed into the first compartment of the first section which is properly labeled. After a packet has been opened, the empty packet is then placed in the corresponding and aligned compartment of the second section. A third aligned compartment in an adjacent third section houses material in which the used needle(s) can be impaled. Accordingly, one has the means for starting with a known number of unopened packets in a first compartment, placing the opened packets as used in an adjacent second compartment, and impaling the used needles in the adjacent third compartment, thus providing a pre-determined arrangement and providing means for a quick and reliable needle count at any time during the procedure.

The use of this monitoring apparatus provides numerous advantages. For instance, a sufficient number of the various types of suture and needles as required in the particular type of surgery can be organized prior to the operation, freeing the circulating nurse to perform other duties. A quick and reliable needle count can be made at any time, thus providing an opportunity for continuous monitoring since the needles are no longer scattered on the tray. The accuracy of such counts is improved since the open packets are organized and grouped as well as the still sealed packets and the used needles. The whole operation is rendered more efficient, in that the scrub nurse has at her disposal a suture container and a disposal chamber which can be kept separate from all other materials on her tray and is easily accessible. Further at end of the procedure this organizer apparatus can be removed from the O.R., enclosed in a gas-permeable cover, and placed in the gas sterilizer; by this means opened suture materials in their packets can be re-used instead of being discarded which is a considerable cost containment.

The various features of novelty which characterize the invention are pointed out with particularity in the claims annexed to and forming a part of this specification. For a better understanding of the invention, its operating advantages and specific objects obtained by its use, reference should be had to the accompanying drawings and descriptive matter in which there is illustrated and described a preferred embodiment of the invention.

BRIEF DESCRIPTION OF THE DRAWINGS

FIG. 1 generally depicts a front elevation view of the apparatus of the present invention;

FIG. 2 shows a top plan view of the apparatus taken along line 2—2 of FIG. 1;

FIG. 5 shows the apparatus in a container.

BEST MODE FOR CARRYING OUT THE INVENTION

Figure 4:
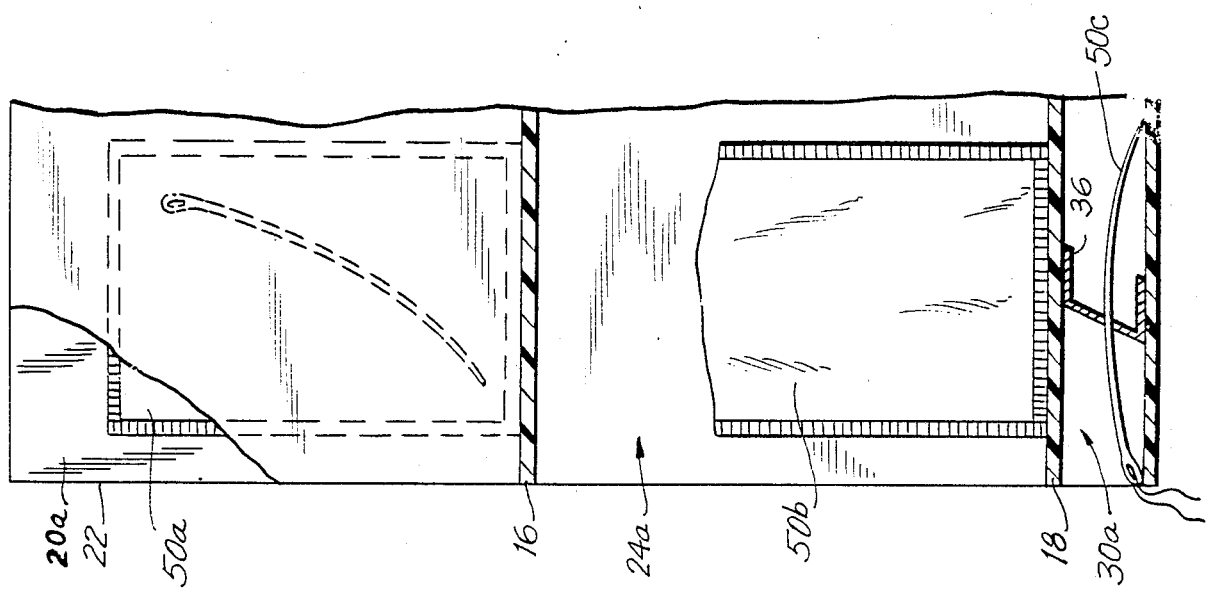
FIG. 4 shows a section taken along 4—4 of FIG. 2.

The present invention is an apparatus and method for organizing, containing and monitoring suture needles. Referring generally to FIGS. 1, 2 and 4, an apparatus 10 is comprised of a housing 11 defining an upper or first section 12 and a lower or second cylindrical section 14 which are co-extensive but separated by a divider or floor 16. Upper section 12 is divided into a plurality of compartments 20 formed by a plurality of blades 22 whose center edges are parallel to one another and generally perpendicularly disposed to divider 16. Section 12 may be roofless to provide for top access to compartments 20. Lower section 14 is likewise divided into a plurality of compartments 24 defined by blades 26 whose outer edges are also in parallel relationship to one another and generally perpendicularly disposed with respect to divider 16 and to lower floor 18. The blades 22 and 26 extend generally radially from a centrally located pole 28 which may be cylindrical or polygonal in section. The blades may be permanently or removeably attached to pole 28, and may be formed with rounded or beaded exposed edges to prevent injury to operating room personnel while stacking or removing the packets. The underside of floor 18 supports a third section 28 of compartments 30, each aligned with an adjacent compartment in the second section. Compartments 30 comprise a needle bank, each containing a quantity of permeable and clinging material such as cloth or styrofoam. Typical label 32 circumferentially spans a plurality of blades to show the designation of suture packets contained in special compartments.

It is an important feature of the invention that corresponding compartments 20, 24 and 30 are aligned. While these compartments are shown in the FIG. 1 embodiment in vertical alignment, it will be appreciated that the alignment may be horizontal or otherwise.

Apparatus 10 is rotabably secured to a shaft 38 by collar 40 which houses a bearing (not shown). A bracket section 42 consisting of a lower and upper arms 44 and 46 respectively and a fastener 48 are preferably positioned at a lower section of shaft 38. The bracket section 42 is adaptable for attaching the apparatus to a surface such as a table or cabinet (not shown).

Compartments 20 are appropriately stocked with suture packets 50 representatively depicted as 50a in FIG. 1 in compartment 20a. In use the unopened packet 50a is withdrawn, opened and the needle and suture are removed. The empty packet 50b is placed in compartment 24a. Later the surgeon returns the used needle 50c to the scrub nurse who impales it in the aligned needle bank material 36 in compartment 30a. Hence the progression of the suture packet proceeds from the unopened packet 50a in section 20a, to the opened packet 50b in 24a, with the used needle 50c impaled in the needle bank 30a permitting a triple visual check at any time.

Preferably the dimensions of compartments 20 and 24 are sufficient to easily receive a plurality of suture packets. Typical dimensions for these compartments are 2½ inches high by 1 inch wide × 5 inches deep, for containers up to twelve packets in each compartment.

While apparatus or housing 10 is freely rotatable, it will be appreciated that a drive means (not shown) may be housed in shaft 38 to rotate the housing 11 at an appropriate and controlled speed to provide ready access to any desired suture packet.

FIG. 1 depicts the apparatus as a vertically disposed cylinder. It will be appreciated that neither the orientation nor the geometry is limiting. For instance apparatus 10 could be polygonal with the number of faces depending on the number of different types of sutures which are anticipated for the particular operation.

Figure 3:
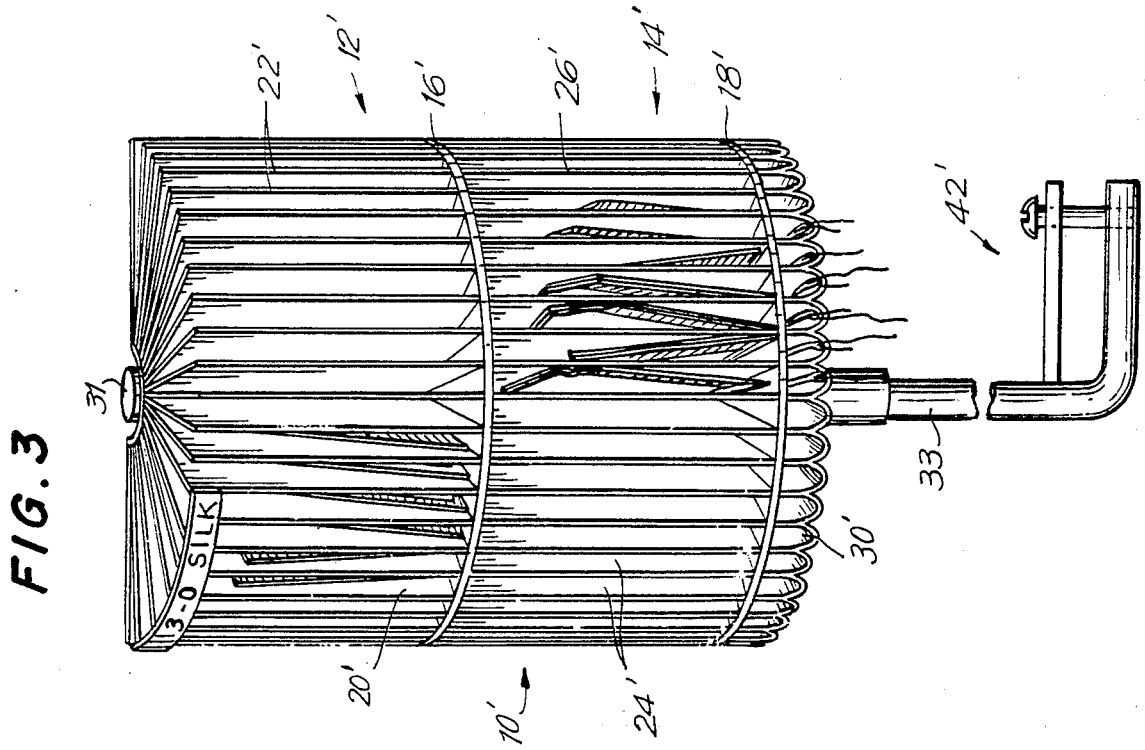
FIG. 3 shows a front view of another embodiment of this invention.

FIG. 3 depicts an alternate embodiment 10' of the apparatus having an upper section 12' and lower section 14' with vertically disposed blades 22' and 26' to form compartments 20' and 24' respectively. Upper and lower sections 12' and 14' are separated by floor divider 16', and lower section 14' is bounded at its lower area by floor 18'. Pockets 30' depend from the underside of floor 18' and house needle bank 34'. In this embodiment post 31 supports the housing by rear plate 29. A shaft 33 engages post 31 and terminates in bracket 42' for attachment to a table or surface. It will be appreciated that a reversing motor and housing can be utilized with this embodiment of the invention as for that depicted in FIG. 1.

FIG. 5 illustrates the apparatus of FIG. 1 within a gas-permeable container 60. After O.R. procedures are completed a suture organizer apparatus with some opened needle packets and other still sealed packets can be closed in the container, gas sterilized via the perforations 51 in container 50, and subsequently returned to the O.R., with an obvious reduction in waste of sutures and needles which are otherwise discarded because sterility was broken.

The method of practicing the invention to monitor suture needles comprises grouping the unopened suture packets in the appropriately provided compartments, withdrawing and opening a selected packet, removing the suture and needle and placing the opened packet in an aligned compartment of an adjacent section of the housing, and lastly, when the surgeon has finished using the needle, returning such needle to the appropriate nurse who impales it in the aligned needle bank. Comparison of the number of opened packets with the number of needles in the bank provides a quick and accurate indication of a correct needle count. Further examination of the remaining unopened packets provides verification of the count. Accordingly, the likelihood of losing track of a needle or miscounting needles is greatly reduced. Since all of the suture packets, opened and unopened, as well as the needles, are organized, aligned and concentrated, the possibilities of needles being misplaced, or opened packets being counted twice, are reduced.

The terms and expressions which have been employed herein are used as terms of description and not of limitation, and there is no intention in the use of such terms and expressions of excluding any equivalents of the features shown and described or portions thereof, it being recognized that various modifications are possible within the scope of the invention.

I claim:

1. A suture organizer apparatus for use with sealed packets of surgical needles and sutures, opened packets for said needles and sutures, and used needles, the apparatus formed as a housing comprising three sections separated from each other by walls with at least first and second compartments in each section, the compartments separated from each other by partitions, the first compartments in all sections being mutually aligned, the second and further compartments in all sections being similarly aligned respectively, and each compartment in the first and second sections comprising walls defining a space with an opening for receiving at least one of said packets containing at least one surgical needle and suture, each compartment in said third section comprising walls defining a space with an opening and an absorbent material traversing said space, said material being impalable to cling to a needle impaled therein.

2. Apparatus according to claim 1 wherein said first, second and third sections are vertically stacked with said first section on top and said third section on bottom.

3. Apparatus according to claim 2 wherein each of said sections is generally cylindrical and coaxial with the others, and said compartments are circumferentially positioned about a vertical central axis with the opening of each compartment facing radially outward.

4. Apparatus according to claim 2 wherein each compartment in said first and second sections defines a space approximately 2½ inches high by 5 inches deep and at least 3/32 inches wide.

5. Apparatus according to claim 4 wherein each compartment in said first and second sections is about one inch wide.

6. Apparatus according to claim 1 wherein said absorbent material comprises a plastic.

7. Apparatus according to claim 1 further comprising a support stand having an upper part on which said housing is rotatably secured.

8. Apparatus according to claim 7 further comprising a mounting means at the bottom of said support stand.

9. Apparatus according to claim 3 wherein each compartment of said third section defines a space approximately 5" deep by at least ½" high and at least ½" wide.

10. Apparatus according to claim 2 wherein each of said sections is a generally semi-circular portion of a cylinder, said portions being coaxial, and said compartments are circumferentially positioned about a vertical, central axis with the opening of each compartment facing radially outward.

11. Apparatus according to claim 1 wherein said first, second and third sections are arranged horizontally with said second section between and closely adjacent said first and third sections.

12. Apparatus according to claim 3 wherein said first and second sections are separated by a first common wall and said second and third sections are separated by a second common wall, and each two adjacent compartments are separated by a single radially extending partition.

* * * * *